(12) United States Patent
Alarcon et al.

(10) Patent No.: US 7,629,172 B2
(45) Date of Patent: Dec. 8, 2009

(54) ENTRAPPED BINDING PROTEIN AS BIOSENSORS

(75) Inventors: Javier Alarcon, Durham, NC (US); Christopher J. Knors, Raleigh, NC (US); J. Bruce Pitner, Durham, NC (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 747 days.

(21) Appl. No.: 10/949,557

(22) Filed: Sep. 27, 2004

(65) Prior Publication Data

US 2005/0042704 A1 Feb. 24, 2005

Related U.S. Application Data

(63) Continuation of application No. 10/039,833, filed on Jan. 4, 2002, now abandoned.

(51) Int. Cl.
G01N 33/48 (2006.01)
(52) U.S. Cl. ............... 436/95; 436/86; 436/164; 436/172; 435/14; 435/287.1; 435/817
(58) Field of Classification Search ............ 436/86, 436/95, 164, 172; 435/7.2, 14, 287.1, 817
See application file for complete search history.

(56) References Cited

U.S. PATENT DOCUMENTS

| | | | |
|---|---|---|---|
| 4,160,698 A | 7/1979 | Miyairi et al. | |
| 4,269,941 A | 5/1981 | Ichimura | |
| 4,703,756 A | 11/1987 | Gough et al. | |
| 5,001,054 A | 3/1991 | Wagner | |
| 5,165,407 A | 11/1992 | Bindra et al. | |
| 5,200,334 A | 4/1993 | Dunn et al. | |
| 5,226,902 A | 7/1993 | Bae et al. | |
| 5,292,801 A | 3/1994 | Avnir et al. | |
| 5,298,022 A | 3/1994 | Bernardi | |
| 5,300,564 A | 4/1994 | Avnir et al. | |
| 5,342,789 A | 8/1994 | Chick et al. | |
| 5,436,161 A | 7/1995 | Bergstrom et al. | |
| 5,445,920 A | 8/1995 | Saito | |
| 5,501,836 A | 3/1996 | Myerson | |
| 5,517,313 A | 5/1996 | Colvin | |
| 5,577,137 A | 11/1996 | Groger et al. | |
| 5,650,311 A | 7/1997 | Avnir et al. | |
| 5,817,493 A | 10/1998 | Reetz et al. | |
| 5,824,526 A | 10/1998 | Avnir et al. | |
| 5,882,494 A | 3/1999 | Van Antwerp et al. | |
| 5,894,351 A | 4/1999 | Colvin | |
| 5,910,661 A | 6/1999 | Colvin | |
| 6,002,954 A * | 12/1999 | Van Antwerp et al. | 600/317 |
| 6,016,689 A | 1/2000 | Bright et al. | |
| 6,080,402 A | 6/2000 | Reetz et al. | |
| 6,197,534 B1 | 3/2001 | Lackowicz et al. | |
| 6,277,627 B1 | 8/2001 | Hellinga | |
| 6,288,214 B1 | 9/2001 | Hook et al. | |
| 6,319,852 B1 | 11/2001 | Smith et al. | |
| 6,403,337 B1 | 6/2002 | Bailey et al. | |
| 6,432,723 B1 | 8/2002 | Plaxco et al. | |
| 6,455,222 B1 | 9/2002 | Fukino et al. | |
| 6,462,162 B2 | 10/2002 | Van Antwerp et al. | |
| 6,475,750 B1 | 11/2002 | Han et al. | |
| 6,495,352 B1 | 12/2002 | Brinker et al. | |
| 6,497,729 B1 | 12/2002 | Moussy et al. | |
| 6,521,446 B2 | 2/2003 | Hellinga | |
| 6,751,491 B2 | 6/2004 | Lew et al. | |
| 2002/0004217 A1 | 1/2002 | Hellinga | |
| 2003/0153026 A1 | 8/2003 | Alarcon et al. | |
| 2004/0234962 A1 | 11/2004 | Alarcon et al. | |
| 2005/0042704 A1 | 2/2005 | Alarcon et al. | |
| 2005/0112685 A1 | 5/2005 | Amiss et al. | |

FOREIGN PATENT DOCUMENTS

| | | |
|---|---|---|
| EP | 409033 | 4/1992 |
| EP | 775669 B1 | 5/2001 |
| JP | 60159643 | 8/1987 |
| JP | 4215054 | 3/1992 |
| JP | 60029657 | 8/1992 |
| JP | 2248852 | 12/1997 |
| JP | 2120655 | 1/1998 |
| WO | WO 0059370 | 10/2000 |

OTHER PUBLICATIONS

Wenner, Brett R., Douglass, Phillip M., et al; Genetically Designed Biosensing Systems for High-Throughput Screening of Pharmaceuticals, Clinical Diagnostics, and Environmental Monitoring; Proc. SPIE (2001), vol. 4252: 59-70.

Hisano et al., Entrapment of islets into reversible disulfide hydrogels, J. Biomed. Mater. Res. 40, pp. 115-123,1998.

Wang et al., Amperometric Glucose Biosensor Based on Sol-Gel Organic-Inorganic Hybrid Material, Anal. Chem., 1998, 70, No. 15, 3170-3174.

Wolfbeis et al., Sol-gel based glucose biosensors enploying optical oxygen transducers, and a method for compensating . . . , Biosensors & Bioelectronics, 15, 2000, 69-76.

Yao & Takashima, Amperometric biosensor with a composite membrane of sol-gel derived enzyme film and electrochemically . . . , Biosensors & Bielectronics, 13, 1, pp. 67-73, 1998.

Bhatia et al., Optical Fiber Long-Period Grating Sensors, Optics Letters 1996, 21:692-694.

Blair et al., Fiber Optic Sensor for Ca2+ Based on an Induced Change in the Conformation on the Protein Calmudulin, Anal. Chem., 1994, 66: 300-02.

Braun et al., Biochemically Active Sol-Gel Glasses: The Trapping of Enzymes, Materials Letters 1990, 10: 1-5.

(Continued)

Primary Examiner—Lyle A Alexander
(74) Attorney, Agent, or Firm—Morgan, Lewis & Bockius LLP (57) ABSTRACT

The invention is directed to entrapped mutated binding proteins, mutated binding proteins containing reporter groups, compositions of mutated binding proteins containing reporter groups in analyte permeable matrixes, and their use as analyte biosensors both in vitro and in vivo.

28 Claims, 4 Drawing Sheets

OTHER PUBLICATIONS

Chen et al., A poly(N-isopropylacrylamide-co-N-acryloxysuccinmide- co-2-hydoxyethyl methacrylate) composite hydrogel . . . , Enzyme and Microbial Technology 2000, 26: 359-67.

Galan-Vidal et al, Glucose biosensor based on a reagentless graphite-epoxy screen-printable biocomposite, Sensors and Actuators, B: Chemical 1997, B45: 55-62.

Gautier et al., Cofactor-containing Bioluminescent fiberoptic sensor—new developments with . . . Analytica Chimica ACTA, 1991, 255: 253-258.

Gautier et al., Reagentless bioluminescent sensor for NADH, Analytical Letters, 1994, 27: 2055-2069.

Gilardi et al., Engineering the Maltose Binding Protein for Reagentless Fluorescence Sensing, Anal. Chem. 1994, 66 21: 3840-3847.

Gowda et al., Development of an Implantable skin port sensor for use as an in-vivo optical glucose sensing platform, Proc. SPIE 2001, 4263: 11-19.

Gruber et al., Preparation of Thiol-Reactive cy5 Derivatives from Commercial Cy5 Succinimidyl Ester, Bioconjugate Chem., 2000, 11: 161-166.

Baker et al., Effects of Poly(Ethylene Glycol) Doping on the Behavior of Pyrene, Rhodamine 6g, and Acrylodan-Labeled Bovine . . . , Jrnl. Of Sol-Gel Sci. and Tech. 1998, 11, 43-54.

Dave et al., Encapsulation of Proteins in Bulk and Thin Film Sol-Gel Matrices, Jrnl of Sol-Gel Sci. and Tech., 1997, 8, 629-634.

Zusman et al., Doped Sol-Gel Glasses As Chemical Sensors, J. Non-Crystalline Solids, 1990, 122, 107-109.

Avnir et al., Enzymes and Other Proteins Entrapped in Sol-Gel Materials, Chemistry of Materials 1994, 6, 1605-1614.

Avnir et al., Encapsulation of Organic-Molecules and Enzymes in Sol-Gel Glasses . . . , ACS Symposium Series 1992, 499, 384-404.

Gill et al., Encapsulation of Biologicals Within Silicate, Siloxane, and Hybrid Sol-Gel Polymers: An Efficient and . . . , Jrnl. of the Amer. Chem. Soc., 1998, 120, 8587-8598.

Flora et al., Comparison of Formats for the Development of Fiber-Optic Biosensors Utilizing Sol-Gel Derived Materials . . . , Analyst 1999, 124, 1455-1462.

Zheng et al., Measurement of Fluorescence from Tryptophan to Probe the Environment and Reaction Kinetics . . . , Analy. Chem., 1997, 69, 3940-49.

Lev et al., Organically Modified Sol-Gel Sensors, Analytical Chemistry 1995, 67, A22-A30.

Shtelzer et al., An Optical Biosensor Based Upon Glucose- Oxidase Immobilized in Sol-Gel Silicate Matrix, Biotech. and Applied Biochem., 1994, 19, 293-305.

Gerritsen et al., Biocompability Evaluation of Sol-Gel Coatings for Subcutaneously Implantable Glucose Sensors, Biomaterials 2000, 21, 71-8.

Gill et al., A Novel Sol-Gel Matrices for the Immobilization of Enzymes, Ann NY Acad. Sci. 1996, 799, 697-700.

Flora et al., Effect of Matrix Aging on Behavior of Human Serum Albumin Entrapped in a Tetraethyl Orthosilicate-Derived Glass, Chemistry of Materials, 2001, 13, 4170-4179.

Brennan, Preparation and Entrapment of Fluorescently Labeled Proteins for the Deveopment of Reagentless Optical Biosensors, Journal of Fluorescence 1999, 9, 295-312.

Flora et al., The Effect of Preparation and Aging Conditions on the Internal Environment of Sol-Gel Derived . . . , Can. Jrnl. of Chem.-Revue Can. De Chimie 1999, 77, 1617-1625.

Zheng et al., Improving the Performance of a Sol-Gel Entrapped Metal-Binding Protein by Maximizing Protein Thermal Stability Before Entrapment, Chem. of Mat. 1998, 10, 3974-83.

Flora et al., Fluorometric Detection of Ca2+ Based on an Induced Change in the Conformation and Sol-Gel Entrapped Parvalbumin, Analy. Chem. 1998, 70, 4505-4513.

Zheng et al., Measurement of Intrinsic Fluorescence to Probe the Conformational Flexibility and Thermodynamic Stabilty of a Single Tryptophan . . . , Analyst 1998, 123, 1735-1744.

Dunn et al., Sensors Based on Sol-Gel Encapsulation Methods, Abstracts of Papers of the American Chemical Society 2001, 221, 473-COLL.

Narang et al., Glucose Biosensor Based on a Sol-Gel Derived Platform, Analy. Chem. 1994, 66, 3139-3144.

Ishihara et al., Glucose Induced Permeation Control of Insulin Through a Complex Membrane Consisting of Immobilized Glucose Oxidase, Polymer J., 1984, 16: 625.

Kermis et al., Transport properties of pHEMA membranes for optical glucose affinity sensors, J. Membrane Science, 2002, 5456: 1-12.

Kok et al., Immobilization of acetylcholinestesterase and choline oxidase in/on pHEMA membrane for biosensor construction, J. Biomater. Sci. Polymer Edn., 2001, 12: 1161-76.

Liu et al., Reagentless amperometric biosensors highly sensitive to hydrogen peroxide, glucose and lactose based on n-methy . . . , Analytica Chimca ACTA, 1997, 344: 187-199.

Looger et al., Computational design of receptor and sesnor proteins with novel functions, Nature 2003, 423: 185-190.

Meadows et al., Fiber-Optic Biosensors Based on Fluorescence energy transfer, Talanta, 1998, 35: 145-150.

Mowbray et al., Structure of the periplasmic glucose/galactose receptor of *Salmonella typhimurium*, Receptor 1990 1: 41-54.

O'Neal et al., Implantable biosensors: analysis of fluorescent light propagation through skin, Proc. SPIE 2001, 4263: 20-24.

Quinn et al., Biocompatible, glucose-permeable hydrogel for in-situ coating of implantable biosensors, Biomaterials: 1997, 18: 1665-1670.

Quinn et al., Photo-crosslinked copolymers of 2-hydroxyethyl methacrylate, poly(ethylene glycol) tetra-acrylate and ethylene dimethylacrylate . . . , Biomaterials 1995, 16: 389-96.

Salins et al., A Novel Reagentless Sensing System for Measuring Glucose Based on the Galactose/Glucose-Binding Protein, Analy. Biochem., 2001, 294, 19-26.

Tolosa et al., Glucose Sensor for Low-Cost Lifetime-Based Sensing Using a Genetically Engineered Protein, 1999, vol. 267, 114-120.

Govind, R., Protein Engineered Glucose Sensor, Database FEDRIP on Dialog (R) File 266: NTIS, 00352410, Identifying No. 1R01RR14170-01, Abstract 1998.

Wenner et al., Genetically Biosensing Systems for High-Throughput Screening of Pharmaceuticals . . . Advances in Fluorescence Sensing Technology V, 2001, 4252, 59-70.

Russell et al., A Fluorescence-Based Glucose Biosensor Using Concanavalin A and Dextran Encapsulated in a Poly(ethylene glycol) Hydrogel, Anal. Chem., 1999, 71, 3126-3132.

Sampath et al., Renewable, Reagentless Glucose Sensor Based on Redox Modified Enzyme and Carbon-Silica Composite, Electroanalysis, 1996, 8:1112-1116.

Topoglidis et al., Protein Adsorption on Nanocrystalline TiO2 Films: An Immobilization Strategy for Bioanalytical Devices, Anal. Chem., 1998, 70: 5111-13.

Vyas et al., Sugar and Signal-Transducer Binding Sites of the *Escherichia coli* Galactose Chemoreceptor Protein, Science 1998, 242: 1290-1295.

Zhao et al., Novel Degradable Poly(ethylene glycol) Hydrogel for Controlled Release of Protein, J. Pharm., Sci., 1998, 87: 1450-58.

Marvin et al., Engineering Biosensors by Introducing Fluorescent Allosteric Signal Transducers: Construction of a Novel Glucose Sensor, J. Am. Chem. Soc. 1998, 120 7-11.

* cited by examiner

ENTRAPPED BINDING PROTEIN AS BIOSENSORS

This application is a continuation of U.S. Ser. No. 10/039,833, filed Jan. 4, 2002, now abandoned the contents of which are herein incorporated by reference.

BACKGROUND OF THE INVENTION

1. Field of the Invention

The invention is in the field of biotechnology. Specifically, the invention is directed to entrapped mutated binding proteins, mutated binding proteins containing reporter groups, compositions of mutated binding proteins containing reporter groups in analyte permeable matrixes, and their use as analyte biosensors both in vitro and in vivo.

2. Description of Relevant Art

Monitoring glucose concentrations to facilitate adequate metabolic control in diabetics is a desirable goal and would enhance the lives of many individuals. Currently, most diabetics use the "finger stick" method to monitor their blood glucose levels and patient compliance is problematic due to pain caused by frequent (several times per day) sticks. As a consequence, there have been efforts to develop non-invasive or minimally invasive in vivo and more efficient in vitro methods for frequent and/or continuous monitoring of blood glucose or other glucose-containing biological fluids. Some of the most promising of these methods involve the use of a biosensor. Biosensors are devices capable of providing specific quantitative or semi-quantitative analytical information using a biological recognition element which is combined with a transducing (detecting) element.

The biological recognition element of a biosensor determines the selectivity, so that only the compound which has to be measured leads to a signal. The selection may be based on biochemical recognition of the ligand where the chemical structure of the ligand (e.g. glucose) is unchanged, or biocatalysis in which the element catalyzes a biochemical reaction of the analyte.

The transducer translates the recognition of the biological recognition element into a semi-quantitative or quantitative signal. Possible transducer technologies are optical, electrochemical, acoustical/mechanical or colorimetrical. The optical properties that have been exploited include absorbance, fluorescence/phosphorescence, bio/chemiluminescence, reflectance, light scattering and refractive index. Conventional reporter groups such as fluorescent compounds may be used, or alternatively, there is the opportunity for direct optical detection, without the need for a label.

Biosensors specifically designed for glucose detection that use biological elements for signal transduction typically use electrochemical or calorimetric detection of glucose oxidase activity. This method is associated with difficulties including the influence of oxygen levels, inhibitors in the blood and problems with electrodes. In addition, detection results in consumption of the analyte that can cause difficulties when measuring low glucose concentrations.

A rapidly advancing area of biosensor development is the use of fluorescently labeled periplasmic binding proteins (PBP's). As reported by Cass (*Anal. Chem.* 1994, 66, 3840-3847), a labeled maltose binding protein (MBP) was effectively demonstrated as a useable maltose sensor. In this work MBP, which has no native cysteine residues, was mutated to provide a protein with a single cysteine residue at a position at 337 (S337C). This mutation position was within the binding cleft where maltose binding occurred and therefore experienced a large environmental change upon maltose binding. Numerous fluorophores were studied, some either blocked ligand binding or interfered with the conformational change of the protein. Of those studied IANBD resulted in a substantial increase in fluorescence (160%) intensity upon maltose binding. This result may be consistent with the location of the fluorophore changing from a hydrophilic or solvent exposed environment to a more hydrophobic environment as would have been theoretically predicted for the closing of the hinge upon maltose binding. However this mutant protein and the associated reporter group do not bind diagnostically important sugars in mammalian bodily fluids. Cass also disclosed *Analytical Chemistry* 1998, 70(23), 5111-5113 association of this protein onto TiO2 surfaces, however, the surface-bound protein suffered from reduced activity with time and required constant hydration.

Hellinga, et al. (U.S. Pat. No. 6,277,627), reports the engineering of a glucose biosensor by introducing a fluorescent transducer into a Galactose/Glucose Binding Protein (GGBP) mutated to contain a cysteine residue, taking advantage of the large conformation changes that occur upon glucose binding. Hellinga et al (U.S. Pat. No. 6,277,627) disclose that the transmission of conformational changes in mutated GGBPs can be exploited to construct integrated signal transduction functions that convert a glucose binding event into a change in fluorescence via an allosteric coupling mechanism. The fluorescent transduction functions are reported to interfere minimally with the intrinsic binding properties of the sugar binding pocket in GGBP.

In order to accurately determine glucose concentration in biological solutions such as blood, interstitial fluids, occular solutions or perspiration, etc., it may be desirable to adjust the binding constant of the sensing molecule of a biosensor so as to match the physiological and/or pathological operating range of the biological solution of interest. Without the appropriate binding constant, a signal may be out of range for a particular physiological and/or pathological concentration. Additionally, biosensors may be configured using more than one protein, each with a different binding constant, to provide accurate measurements over a wide range of glucose concentrations as disclosed by Lakowicz (U.S. Pat. No. 6,197,534).

Despite the usefulness of mutated GGBPs, few of these proteins have been designed and examined, either with or without reporter groups. Specific mutations of sites and/or attachment of certain reporter groups may act to modify a binding constant in an unpredictable way. Additionally, a biosensor containing reporter groups may have a desirable binding constant, but not result in an easily detectable signal upon analyte binding. Some of the overriding factors that determine sensitivity of a particular reporter probe attached to a particular protein for the detection of a specific analyte is the nature of the specific interactions between the selected probe and amino acid residues of the protein. It is not currently possible to predict these interactions within proteins using existing computational methods, nor is it possible to employ rational design methodology to optimize the choice of reporter probes. It is currently not possible to predict the effect on either the binding constant or the selectivity based on the position of any reporter group, or amino acid substitution in the protein (or visa-versa).

To develop reagentless, self-contained, and or implantable and or reusable biosensors using proteins the transduction element must be in communication with a detection device to interrogate the signal to and from the transduction element. Typical methods include placing proteins within or onto the surface of optical fibers or planner waveguides using immobilization strategies. Such immobilization strategies include, but are not limited to, entrapment of the protein within semipermeable membranes, organic polymer matrixes, or inorganic polymer matrixes. The immobilization strategy ultimately may determine the performance of the working biosensor. Prior art details numerous problems associated with the immobilization of biological molecules. For example, many proteins undergo irreversible conformational changes, denaturing, and loss of biochemical activity. Immobilized proteins can exist in a large number of possible orientations on any particular surface, for example, with some proteins oriented such that their active sites are exposed whereas others may be oriented such that there active sites are not exposed, and thus not able to undergo selective binding reactions with the analyte. Immobilized proteins are also subject to time-dependent denaturing, denaturing during immobilization, and leaching of the entrapped protein subsequent to immobilization. Therefore problems result including an inability to maintain calibration of the sensing device and signal drift. In general, binding proteins require orientational control to enable their use, thus physical absorption and random or bulk covalent surface attachment or immobilization strategies as taught in the literature generally are not successful.

There have been several reports of encapsulating proteins and other biological systems into simple inorganic silicon matrixes formed by a low temperature sol-gel processing methods, for example, as taught by Brennan, J. D. *Journal of Fluorescence* 1999, 9(4), 295-312, and Flora, K.; Brennan, J. D. *Analytical Chemistry* 1998, 70(21), 4505-4513. Some sol-gel matrixes are optically transparency, making them useful for the development of chemical and bio-chemical sensors that rely on optical transduction, for example absorption or fluorescence spectroscopic methods. However, entrapped or immobilized binding proteins must remain able to undergo at least some analyte induced conformational change. Conformational motions of binding proteins may be substantially restricted in most sol-gel matrixes as taught in the literature. It has been reported that sol-gel entrapped proteins can exhibit dramatically altered binding constants, or binding constants that change over relatively short time periods or under varying environmental conditions. In addition, a time dependence of the protein function while entrapped in the sol-gel matrix has been reported. This time dependence of protein function in sol-gel entrapped matrixes has limited general applicability of sol-gels in biosensors for in vitro as well as in vivo use.

Therefore, there is a need in the art to design additional useful mutated proteins and mutated GGBP proteins generating detectable signals upon analyte binding for use as biosensors, and additionally there is a need for the entrapment of these proteins into analyte-permeable matrixes for interfacing to signal transmitting and receiving elements.

SUMMARY OF THE INVENTION

The invention provides entrapped or encapsulated mutated binding proteins and mutated binding proteins having reporter groups attached thereto, for their use as in vivo or in vitro biosensors. Furthermore the invention provides a glucose biosensor including (a) a mutated binding protein and at least one reporter group attached thereto such that said reporter group provides detectable signal when said mutated binding protein is exposed to glucose and (b) a matrix permeable to analyte where the mutated glucose/galactose binding protein and the reporter group are encapsulated in the matrix.

The invention also provides compositions comprising a mixture including (a) at least one mutated glucose/galactose binding protein and at least one reporter group attached thereto and (b) a hydrogel, dialysis membrane, sol-gel, or combinations thereof to provide for a matrix permeable to analyte wherein the mutated glucose/galactose binding protein and the reporter group are encapsulated in the matrix.

The invention also provides a device including (a) a mutated maltose binding protein (MBP) and at least one reporter group attached thereto such that the reporter group provides a detectable signal when the mutated MBP is bound to maltose and wherein the MBP includes a cysteine present at position 337 and (b) a matrix permeable to maltose wherein the mutated MBP and the reporter group are encapsulated in the matrix.

The invention further provides a device and compositions thereof suitable for in vivo use including (a) a mutated glucose/galactose binding protein and at least one reporter group attached thereto such that the reporter group provides a detectable and reversible signal when the mutated glucose/galactose binding protein is exposed to varying glucose concentrations and (b) a matrix permeable to analyte wherein the mutated glucose/galactose binding protein and the reporter group are encapsulated in the matrix.

DETAILED DESCRIPTION

The term biosensor generally refers to a device that uses specific biochemical reactions mediated by isolated enzymes, immunosystems, tissues, organelles or whole cells to detect chemical compounds, usually by electrical, thermal or optical signals. As used herein a "biosensor" refers to a protein capable of binding to analyte which may be used to detect analyte or a change in analyte concentration by a detector means as herein described.

The term "binding proteins" refers to proteins which interact with specific analytes in a manner capable of transducing or providing a detectable and or reversible signal differentiable either from when analyte is not present, analyte is present in varying concentrations over time, or in a concentration-dependent manner, by means of the methods described. The transduction event includes continuous, programmed, and episodic means, including one-time or reusable applications. Reversible signal transduction may be instantaneous or may be time-dependent providing a correlation with the presence or concentration of analyte is established. Binding proteins mutated in such a manner to effect transduction are preferred.

The term "galactose/glucose binding protein" or "GGBP" or "maltose binding protein" or "MBP" as used herein refers to a type of protein naturally found in the periplasmic compartment of bacteria. These proteins are naturally involved in chemotaxis and transport of small molecules (e.g., sugars, amino acids, and small peptides) into the cytoplasm. For example, GGBP is a single chain protein consisting of two globular α/β domains that are connected by three strands to form a hinge. The binding site is located in the cleft between the two domains. When glucose enters the binding site, GGBP undergoes a conformational change, centered at the hinge, which brings the two domains together and entraps glucose in the binding site. X-ray crystallographic structures have been determined for the closed form of GGBP from *E. coli* (N. K. Vyas, M. N. Vyas, F. A. Quiocho *Science* 1988, 242, 1290-1295) and *S. Typhimurium* (S. L. Mowbray, R. D. Smith, L. B. Cole *Receptor* 1990, 1, 41-54) and are available from the Protein Data Bank (http://www.rcsb.org/pdb/) as 2 GBP and 3 GBP, respectively. The wild type *E. coli* GGBP DNA and amino acid sequence can be found at www.ncbi.nlm.nih.gov/entrez/ accession number D90885 (genomic clone) and accession number 23052 (amino acid sequence). Preferred GGBP is from *E. coli*.

"Mutated binding protein" (for example "mutated GGBP") as used herein refers to binding proteins from bacteria containing amino acid(s) which have been substituted for, deleted from, or added to the amino acid(s) present in naturally occurring protein.

Exemplary mutations of binding proteins include the addition or substitution of cysteine groups, non-naturally occurring amino acids (Turcatti, et al. *J. Bio. Chem.* 1996 271, 33, 19991-19998) and replacement of substantially non-reactive amino acids with reactive amino acids to provide for the covalent attachment of electrochemical or photo-responsive reporter groups.

Exemplary mutations of the GGBP protein include a cysteine substituted for a lysine at position 11 (K11C), a cysteine substituted for aspartic acid at position 14 (D14C), a cysteine substituted for valine at position 19 (V19C), a cysteine substituted for asparagine at position 43 (N43C), a cysteine substituted for a glycine at position 74 (G74C), a cysteine substituted for a tyrosine at position 107 (Y107C), a cysteine substituted for threonine at position 110 (T110C), a cysteine substituted for serine at position 112 (S112C), a double mutant including a cysteine substituted for a serine at position 112 and serine substituted for an leucine at position 238 (S112C/L238S), a cysteine substituted for a lysine at position 113 (K113C), a cysteine substituted for a lysine at position 137 (K137C), a cysteine substituted for glutamic acid at position 149 (E149C), a double mutant including a cysteine substituted for an glutamic acid at position 149 and a serine substituted for leucine at position 238 (E149C/L238S), a double mutant comprising a cysteine substituted for histidine at position 152 and a cysteine substituted for methionine at position 182 (H152C/M182C), a double mutant including a serine substituted for an alanine at position 213 and a cysteine substituted for a histidine at position 152 (H152C/A213S), a cysteine substituted for an methionine at position 182 (M182C), a cysteine substituted for an alanine at position 213 (A213C), a double mutant including a cysteine substituted for an alanine at position 213 and a cysteine substituted for an leucine at position 238 (A213C/L238C), a cysteine substituted for an methionine at position 216 (M216C), a cysteine substituted for aspartic acid at position 236 (D236C), a cysteine substituted for an leucine at position 238 (L238C) a cysteine substituted for a aspartic acid at position 287 (D287C), a cysteine substituted for an arginine at position 292 (R292C), a cysteine substituted for a valine at position 296 (V296C), a triple mutant including a cysteine substituted for an glutamic acid at position 149 and a alanine substituted for a serine at position 213 and a serine substituted for leucine at position 238 (E149C/A213S/L238S), a triple mutant including a cysteine substituted for an glutamic acid at position 149 and a alanine substituted for an arginine at position 213 and a serine substituted for leucine at position 238 (E149C/A213R/L238S).

The entrapped or encapsulated mutated binding proteins of the present invention may be used in an in vitro or in vivo analyte assay which, for example, is capable of following the kinetics of biological reactions involving an analyte or glucose, as well as in clinical assays and food or beverage industrial testing. The concentration of the binding protein in the matrix is preferred to be less than the Kd of the protein with its analyte.

The mutation may serve one or more of several purposes. For example, a naturally occurring protein may be mutated in order to change the long-term stability of the protein; to conjugate the protein to a particular encapsulation matrix, polymer; or to provide binding sites for detectable reporter groups, or to adjust its binding constant with respect to a particular analyte, or combinations thereof.

In the instant invention, analyte and mutated protein act as binding partners. The term "associates" or "binds" as used herein refers to binding partners having a relative binding constant (Kd) sufficiently strong to allow detection of binding to the protein by a detection means. The Kd may be calculated as the concentration of free analyte at which half the protein is bound, or vice versa. When the analyte of interest is glucose, the Kd values for the binding partners are preferably between about 0.0001 mM to about 20 mM.

In the present invention, it has been shown that mutated GGBPs may be used to detect glucose binding by attaching thereto a reporter group which provides a detectable signal upon glucose binding. To "provide a detectable signal", as used herein refers to the ability to recognize a change in a property of a reporter group in a manner that enables the detection of ligand-protein binding. For example, in one embodiment, the mutated GGBPs comprise a detectable reporter group whose detectable characteristics alter upon a change in protein conformation which occurs on glucose binding. In a preferred embodiment, the reporter group is a luminescent label which results in a mutated GGBP with an affinity for glucose producing a detectable shift in luminescence characteristics on glucose binding. The change in the detectable characteristics may be due to an alteration in the environment of the label bound to the mutated GGBP.

The luminescent label may be a fluorescent label or a phosphorescent label. The use of fluorescent labels, which may be excited to fluoresce by exposure to certain wavelengths of light is preferred.

In one embodiment, the reporter group is a fluorophore. As used herein, "fluorophore" refers to a molecule that absorbs energy and then emits light. Non-limiting examples of fluorophores useful as reporter groups in this invention include fluorescein, coumarins, rhodamines, 5-TMRIA (tetramethylrhodamine-5-iodoacetamide), Quantum Red™, Texas Red™, Cy3, N-((2-iodoacetoxy)ethyl)-N-methyl)amino-7-nitrobenzoxadiazole (IANBD), 6-acryloyl-2-dimethylaminonaphthalene (acrylodan), pyrene, Lucifer Yellow, Cy5, Dapoxyl® (2-bromoacetamidoethyl)sulfonamide, (N-(4,4-difluoro-1,3,5,7-tetramethyl-4-bora-3a,4a-diaza-s-indacene-2-yl)iodoacetamide (Bodipy507/545 IA), N-(4,4-difluoro-5, 7-diphenyl-4-bora-3a,4a-diaza-s-indacene-3-propionyl)-N'-iodoacetylethylenediamine (BODIPY® 530/550 IA), 5-((((2-iodoacetyl)amino)ethyl)amino)naphthalene-1-sulfonic acid (1,5-IAEDANS), and carboxy-X-rhodamine, 5/6-iodoacetamide (XRIA 5,6). Preferably, IANBD is used. Many detectable intrinsic properties of a fluorophore reporter group may be monitored to detect glucose binding. Some of these properties which can exhibit changes upon glucose binding include fluorescence lifetime, fluorescence intensity, fluorescence anisotropy or polarization, and spectral shifts of fluorescence emission. Changes in these fluorophore properties may be induced from changes in the fluorophore environment such as those resulting from changes in protein conformation. Environment-sensitive dyes such as IANBD are particularly useful in this respect. Other changes of fluorophore properties may result from interactions with the analyte itself or from interactions with a second reporter group, for example when FRET (fluorescence resonance energy transfer) is used to monitor changes in distance between two fluorophores.

Although the use of fluorescent labels is desired, it is contemplated that other reporter groups may be used. For example, electrochemical reporter groups could be used wherein an alteration in the environment of the reporter will give rise to a change in the redox state thereof. Such a change may be detected using an electrode.

Furthermore, it is envisaged that other spectroscopically detectable labels, for example labels detectable by NMR (nuclear magnetic resonance), may be used The reporter group may be attached to the mutated protein or GGBPs by any conventional means known in the art. For example, the reporter group may be attached via amines or carboxyl residues on the protein. However, especially preferred is covalent coupling via thiol groups on cysteine residues. For example, for mutated GGBP, cysteines located at position 11, position 14, position 19, position 43, position 74, position 107, position 110, position 112, position 113, position 137, position 149, position 152, position 213, position 216, position 238, position 287, and position 292 are preferred in the present invention.

Any thiol-reactive group known in the art may be used for attaching reporter groups such as fluorophores to an engineered or mutated protein's cysteine. For example, an iodoacetamide, bromoacetamide, or maleimide are well known thiol-reactive moieties that may be used for this purpose.

Fluorophores that operate at long excitation and emission wavelengths (for example, about 600 nm or greater excitation or emission wavelengths) are preferred when the molecular sensor is to be used in vivo, for example, incorporated into an implantable biosensor device (the skin being opaque below 600 nm). Presently, there are few environmentally sensitive probes available in this region of the spectrum and perhaps none with thiol-reactive functional groups. However, thiol-reactive derivatives of Cy-5 can be prepared for example as taught by H. J. Gruber, et al, *Bioconjugate Chem.*, (2000), 11, 161-166. Conjugates containing these fluorophores, for example, attached at various cysteine mutants constructed in mutated GGBPs, can be screened to identify which results in the largest change in fluorescence upon glucose binding.

Mutated GGBPs useful in the present invention may be engineered or mutated to have a histidine tag on the proteins N-terminus, C-terminus, or both termini. Histidine fusion proteins are widely used in the molecular biology field to aid in the purification of proteins. Exemplary tagging systems produce proteins with a tag containing about six histidines and preferably such tagging does not compromise the binding activity of the mutated GGBP.

As used herein, "matrix" refers to essentially a three-dimensional environment which has at least one binding protein immobilized for the purpose of measuring a detectable signal from ligand-protein interaction. The relationship between the constituents of the matrix and the binding protein include, but are not limited to covalent, ionic, and Van derWals interactions and combinations thereof. The spatial relationship between the matrix and binding protein includes heterogeneous and homogeneous distribution within and or upon any or all of the matrix volume. The matrix may be comprised of organic, inorganic, glass, metal, plastic, or combinations thereof. The matrix provides for the binding protein transducing element configuration which may be for example, be incorporated at the distal end of a fiber or other small minimally invasive probe to be inserted within the tissue of a patient, to enable an episodic, continuous, or programmed reading to the patient. Information from the transducing element to the patient may be provided, for example, by telemetry, visual, audio, or other means known in the art, for example, as taught in U.S. Pat. Nos. 5,517,313, 5,910,661, 5,894,351, and 5,342,789 as well as in Beach, R. D., et al. *IEEE Transactions on Instrumentation and Measurement* (1999) 48, 6, p. 1239-1245. Information includes electrical, mechanical, and actinic radiation suitable for deriving analyte concentration or change in concentration, as is suitable.

In one aspect of the present invention, the biosensor is used for analyte sensing in vivo. In this aspect, the biosensor is encapsulated into a matrix which may then be used as an implantable device. The "matrix" can be in any desirable form or shape including one or more of disk, cylinder, patch, nanoparticle, microsphere, porous polymer, open cell foam, and combinations thereof, providing it permits permeability to analyte. The matrix additionally prevents leaching of the biosensor. The matrix permits light from optical sources or any other interrogating light to or from the reporter group to pass through the biosensor. When used in an in vivo application, the biosensor will be exposed to a substantially physiological range of analyte and determination or detection of a change in analyte concentration would be desired whereas the determination or detection includes continuous, programmed, and episodic detection means. Thus, the envisaged in vivo biosensor of the present invention comprises at least one mutated binding protein in an analyte permeable entrapping or encapsulating matrix such that the mutated binding protein provides a detectable and reversible signal when the mutated binding protein is exposed to varying analyte concentrations, and the detectable and reversible signal can be related to the concentration of the analyte. The implantable biosensors may, in some embodiments, be implanted into or below the skin of a mammal's epidermal-dermal junction to interact with the interstitial fluid, tissue, or other biological fluids. Information from the implant to the patient may be provided, for example, by telemetry, visual, audio, or other means known in the art, as previously stated.

Preferably, the matrix is prepared from biocompatible materials or incorporates materials capable of minimizing adverse reactions with the body. Adverse reactions for implants include, inflammation, protein fouling, tissue necrosis, immune response and leaching of toxic materials. Such materials or treatments are well known and practiced in the art, for example as taught by Quinn, C. P.; Pathak, C. P.; Heller, A.; Hubbell, J. A. *Biomaterials* 1995, 16(5), 389-396, and Quinn, C. A. P.; Connor, R. E.; Heller, A. *Biomaterials* 1997, 18(24), 1665-1670.

The biosensor may be encapsulated into a matrix derived substantially from a hydrogel. The polymer portion of the hydrogel may contain functionality which is suitable for hydrogen bonding or covalent coupling (e.g. hydroxyl groups, amino groups, ether linkages, carboxylic acids and esters and the like) to either the protein or reporter group.

Numerous hydrogels may be used in the present invention. The hydrogels may be, for example, polysaccharides such as agarose, dextran, carrageenan, alginic acid, starch, cellulose, or derivatives of these such as, e.g., carboxymethyl derivatives, or a water-swellable organic polymer such as, e.g., polyvinyl alcohol, polyacrylic acid, polyacrylamide, polyethylene glycol, copolymers of styrene and maleic anhydride, copolymers of vinyl ether and maleic anhydride and derivates thereof. Derivatives providing for covalently crosslinked networks are preferred. Synthesis and biomedical and pharmaceutical applications of hydrogels based on, comprising polypeptides, have been described by a number of researchers. (See, e.g. "Biosensors Fundamentals and Applications", edited by A. D. F. Turner, I. Karube and G. S. Wilson; published from Oxford University Press, in 1988). An exemplary hydrogel matrix derived from a water-soluble, UV crosslinkable polymer comprises poly(vinyl alcohol),N-methyl-4(4'-formylstyryl)pyridinium methosulphate acetal (CAS Reg. No. [107845-59-0]) available from PolyScience Warrington, Pa.

In one embodiment of the encapsulation process, one or more hydrogels in water is added the mutated binding protein in an aqueous buffer solution having a pH in the range of about 4 to about 10 depending on the protein. Subsequent curing of the matrix, for example crosslinking, provides physical form. Using this technique and a conventional fabrication process (e.g. block casting, reverse emulsion polymerization, screen or contact printing, fluid-bed coating and dip or spin coating) one can obtain matrixes in various configurations (e.g. granulates, nanoparticles, microparticles, monoliths, and thick and thin films) suitable for in vitro and in vivo use.

The matrix may, in one embodiment, be comprised of modified sol-gels. Modified sol-gels includes at least partial cured (or gelled) preparations comprised of permeable metal oxide glass structures containing in addition to the sol-gel precursor materials, preferably one or more organic components which hydrolytically condense along with the sol-gel precursor such that the resultant sol-gel matrix imparts properties suitable for, by example, implantation. Suitable properties include low volume shrinkage over time, resistance to cracking and other physical defects, maintenance of protein function, and compatibility with the protein and or reporter group, and compatibility with the animal or subject to which it may be implanted. Suitable organic materials include polyols such as glycerol, ethylene glycol, propylene glycol, polyethylene glycol, and the like for example, as taught by Gill and Ballesteros *Journal of the American Chemical Society* 1998, 120(34), 8587-8598. It is understood that those skilled in the art can appreciate the attributes described are generally not predictable for a given protein/sol-gel/reporter group combination, thus optimization of sol-gel precursor, organic component and protein solution materials may be expected for any given binding protein-reporter pair. It has been found by the applicants that such optimization may provide for unexpected enhanced signal, shifted binding constants, improved physical performance attributes of the matrix, and combinations thereof relative to that of other matrixes or aqueous solutions thereof. Optimization of performance attributes of the protein-reporter pair and functional performance attributes of the matrix encapsulating same may be achieved, for example, by way of combinatorial methods or other statistical based design methods known in the art.

Sol-gel matrixes useful for the present invention include material prepared by conventional, well-known sol-gel methods and include inorganic material, organic material or mixed organic/inorganic material. The materials used to produce the sol-gel can include, but are not limited to, aluminates, aluminosilicates and titanates. These materials may be augmented with the organically modified silicates (Ormosils) and functionalized siloxanes, to provide an avenue for imparting and manipulating hydrophilicity and hydrophobicity, ionic charge, covalent attachment of protein, and the like. As used herein the term "hydrolytically condensable siloxane" refers to sol-gel precursors having a total of four substituents, at least one, preferably two, and most preferably three or four of the substituents being alkoxy substituents covalently bound to silicone through oxygen and mixtures thereof. In the case of three, two, and one alkoxy substituent precursors, at least one of the remaining substituents preferably is covalently bound to silicone through carbon, and whereas the remaining substitutent contains organic functionality from alkyl, aryl, amine, amide, thiol, cyano, carboxyl, ester, olefinic, epoxy, silyl, nitro, and halogen.

In one embodiment of the encapsulation process, one or more of hydrolytically condensable siloxane is hydrolyzed in water, either spontaneously or under acid or base catalysis to form derivatives with an organic polyol component present in a molar amount relative to the hydrolytically condensable siloxane up to about 10:1 to 1:10, preferably to about 5:1 to 1:5, and most preferably to about 1:1. To this mixture, prior to final gellation, is added the mutated binding protein in an aqueous buffer solution having a pH in the range of about 4 to about 10 depending on the protein. At least partial condensation reactions give rise to the final matrices.

In another embodiment, the hydrolytically condensable siloxane hydrolyzed in water, either spontaneously or under acid or base catalysis to form derivatives with the organic polyol, is mixed with a water soluble polymer component. Suitable water soluble polymers include polyvinyl alcohol (PVA), poly-(maleic acid co-olefin) sodium salt (PMSA), poly-(vinylsulfonic acid) sodium salt (PVSA), and polyvinyl pyrollidone (PVP). Poly-(maleic acid co-olefin) includes copolymers of maleic anhydride with styrene, vinyl ether, and C1-C8 olefins and salts thereof, for example, sodium, potassium, ammonium, tetraakylammonium, and the like. Preferably, the water soluble polymer component is from 0 to about 30% by weight of the sol-gel composition.

In another embodiment the hydrolytically condensable siloxane hydrolyzed in water, either spontaneously or under acid or base catalysis to form derivatives with the organic polyol, is mixed with one or more functionalized silicone additives (FSA) in amounts from 0 to about 0.6% mole ratios to hydrolytically condensable siloxane. Exemplary FSA's include alkyl derivatives: for example, methyltrimethoxysilane (MTMOS): amine derivatives: for example, 3-aminopropyl triethoxysilane (ATEOS); and bis silane derivatives: for example, (bis(3-methyldimethoxysilil)propyl) polypropylene oxide (BIS).

In another embodiment, both the water soluble polymer component and the functionalized silicone additive are mixed together with the hydrolytically condensable siloxane hydrolyzed in water, either spontaneously or under acid or base catalysis to form derivatives with the organic polyol, to provide for a matrix suitable for entrapment or encapsulation of the binding protein. Using the afore-mentioned sol-gel technique and a conventional fabrication process (e.g. block casting, reverse emulsion polymerization, screen or contact printing, fluid-bed coating and dip or spin coating) one can obtain aerogel- or xerogel-matrixes in various configurations (e.g. granulates, nanoparticles, microparticles, monoliths, and thick and thin films) suitable for use in vitro and in vivo.

In another embodiment the matrix may be formed from dialysis membranes. The dialysis membranes can be constructed to physically encapsulate or entrap the protein. Covalent attachment to the membrane is considered within the scope of the as described embodiment. The membrane should be chosen based on its molecular weight cut-off such that analytes of interest can readily permeate the membrane whilst high molecular weight materials would be restricted from entering, or in the case of the mutated binding proteins, leaving the membrane matrix. The molecular weight cut-off required would be such as to meet the afore-mentioned requirement and is within the skill of one familiar with this art. Typically, membranes having molecular weight cut-off between about 1000 to about 25,000 Daltons are suitable. Using this technique, matrixes in various configurations and shapes suitable for use in vitro and in vivo can be prepared.

It is also contemplated that matrixes containing the binding protein and reporter group be combinations of one or more hydrogel, sol-gel, and dialysis membranes. For example, a protein entrapped or encapsulated within a hydrogel or sol gel can be placed within a dialysis membrane of a suitable shape and size as would provide for implantation within a subject, or to manipulate mass-transport properties or permeability of the analytes with respect to the matrix.

The matrix entrapped or encapsulated binding protein biosensors of this invention are capable of measuring or detecting micromolar ($10^{-6}$ molar) to molar analyte concentrations without reagent consumption. In some embodiments, their sensitivity to analyte may enable the biosensors to be used to measure the low analyte concentrations known to be present in low volume samples of interstitial fluid. The implantable biosensors may, in some embodiments, be implanted into or below the skin of a mammal's epidermal-dermal junction to interact with the interstitial fluid, tissue, or other biological fluids. The binding protein biosensors of the present invention provide for the means to monitor analyte continuously, episodically, or "on-demand" as would be appropriate to the user or to the treatment of a condition.

In other embodiments, the biosensors sensitivity to analyte (for example glucose) is such that they may be used to test blood analyte levels or the concentration of analyte in a biological solution or other solution may be determined. As used herein, a "biological solution" includes but is not limited to blood, perspiration, and or ocular or interstitial fluid including combinations thereof.

EXAMPLES

The following examples illustrate certain preferred embodiments of the instant invention, but are not intended to be illustrative of all embodiments. Labeled mutated maltose binding protein S337C MBP with fluorophore reporter probe NBD used herein in accordance with the procedure set forth by Cass, A. et al. (*Anal. Chem.* 1994, 66, 3840-3847). Fluorescence emission spectra of mutated, labeled protein was measured using an SLM Aminco fluorimeter (Ontario, Canada) with slit settings of 8 and 4 for excitation and settings of 5 and 5 on the MC250 emission monochromator to compare the ligand-binding performance of the entrapped fluorophore-labeled proteins in various matrixes to the performance of the same proteins in solution. The initial fluorescence emission intensity is defined as $I_o$. The relative ratio of the emission intensity maxima in the presence of the protein's respective ligand ($I_f$) to the ligand's absence ($I_o$) is defined as ΔF.

Binding constants were determined by titration of increasing concentrations of glucose into a protein solution with mixing following each addition of glucose. Slit settings were the same as listed above. The Kd was determined from the following relationships as adapted from Pisarchick and Thompson (1990):

$$F = F_{inf} + \frac{F_0 - F_{inf}}{1 + x/Kd} \quad (1)$$

where F is fluorescence intensity, $F_{inf}$ is fluorescence at infinity, $F_0$ is fluorescence at zero glucose, and x is the free concentration of glucose ($[Glc]_{free}$) as determined by the relationship:

$$[Glc]_{free} = \frac{[GLC]_{tot} - [Prot]_{tot} - Kd + \sqrt{([Glc]_{tot} - [Prot]_{tot} - Kd)2 + 4*[Glc]_{tot}*Kd}}{2} \quad (2)$$

where $[Glc]_{tot}$ and $[Prot]_{tot}$ are the total concentrations of glucose and protein, respectively.

Example 1

This example describes the method for the expression and purification of mutant Proteins Without Histidine Tags. GGBP is coded by the Mg1B-1 gene in *E. coli*. This protein was altered by introducing the amino acid cysteine at various positions through site-directed mutagenesis of the Mg1B-1 gene. These proteins were then expressed in *E. coli* and purified.

Cassette mutagenesis of Mg1B-1 was accomplished as follows. The wild-type Mg1B-1 gene was cloned into a pTZ18R vector (Dr. Anthony Cass, Imperial College, London, England). Mutant plasmids were generated from this parent plasmid using cassette mutatgenesis producing randomized amino acid sequences, essentially as described by Kunkel (1991) and cloned in *E. coli* JM109 (Promega Life Science, Madison, Wis.). Mutant plasmids were identified by sequencing. The mutant protein was induced in JM109 and purified as described below. An *E. coli* JM109 colony containing the mutant plasmid was grown overnight at 37° C. with shaking (220 rpm) in LB broth containing 50 µg/mL ampicillin (LB/Amp). The overnight growth was diluted 1:100 in 1 L fresh LB/Amp and was incubated at 37° C. with shaking until the $OD_{600}$ of the culture was 0.3-0.5. Expression of the mutant was induced by the addition of 1 mM IPTG (Life Technologies, Gaithersburg, Md.) final concentration with continued incubation and shaking at 37° C. for 4-6 hours. The cells were harvested by centrifugation (10,000×g, 10 min, 4° C.).

The mutant protein was harvested by osmotic shock and was purified by column chromatography. The cell pellet was resuspended in a sucrose buffer (30 mM Tris-HCL pH 8.0, 20% sucrose, 1 mM EDTA), incubated at room temperature for 10 min, and then centrifuged (4000×g, 15 min, 4° C.). The supernatant was poured off and kept on ice. The cell pellet was resuspended, and 10 mL ice cold, sterile deionized $H_2O$ was repeated, and the suspension was incubated on ice and centrifuged. The remaining supernatant was pooled with the other collected supernatants and was centrifuged once again (12,000×g, 10 min, 4° C.). The pooled shockate was filtered through a 0.8 µm and then a 0.45 µm filter. Streptomycin sulfate (Sigma Chemical Co., St. Louis, Mo.), 5% w/v, was added to the shockate and was stirred once for 30 min followed by centrifugation (12,000×g, 10 min, 4° C.). The shockate was then concentrated using the Amicon Centriprep 10 (10,000 MWCO) filters (Charlotte, N.C.) and dialyzed overnight against 5 mM Tris-HCl pH 8.0, 1 mM $MgCl_2$. The dialyzed shockate was centrifuged (12,000×g, 30 min, 4° C.).

The resulting supernatant was added to a pre-equilibrated DEAE Fast Flow Sepharose column (Amersham Pharmacia Biotech, Piscataway, N.J.) at 0.5 mL/min. The column was washed with 5-10 column volumes. A linear gradient from 0-0.2 M NaCl was applied to the column and fractions were collected. The mutant protein containing fractions were identified by SDS-PAGE with Coomassie Brilliant Blue staining (mw. Approx. 32 kDa). The fractions were pooled and dialyzed overnight (4° C.) against phosphate buffered saline (PBS) or 10 mM ammonium bicarbonate (pH 7.4) concentrated using Amicon Centriprep 10 filters, and stored at 4° C. or −20° C. with glycerol. The ammonium bicarbonate dialyzed protein was lyophilized.

Example 2

This example describes the expression and purification of mutant GGBPs containing Histidine Tags. GGBP mutants were engineered by either site-directed mutagenesis or the cassette mutagenesis. Site-directed mutagenesis (QuikChange, Stratagene, La Jolla, Calif.) was performed to alter individual amino acids in the pQE70 vector by replacing one amino acid with another, specifically chosen amino acid. The cassette mutagenesis method (Kunkel 1991) was performed to randomize amino acids in a specified region of the GGBP gene. The mutated cassettes were then subcloned into the pQE70 expression vector. The pGGBP-His plasmid contained the GGBP gene cloned into the pQE70 expression vector (Qiagen, Valencia, Calif.). This construct places six histidine residues on the C-terminus of the GGBP gene. *E. coli* strain SG13009 was used to over express mutant GGBP-His following standard procedures (Qiagen). After over expression of a 250 mL culture, the cells were collected by centrifugation (6000 rpm) and resuspended in 25 mL bug-buster (Novagen, Madison, Wis.). Lysozyme (25 mg was added to the lysate and the mixture was gently mixed at room temperature (RT) for 30 min. Clear lysate was produced by centrifugation (6000 rpm) and to this, 0.5 ml imidizole (1 M) and 3 ml of Ni-NTA beads (Qiagen) was added. After 30 minutes of gently mixing at RT, the mixture was centrifuged (6000 rpm) and the lysate removed. The beads were washed with 25 ml of solution (1M NaCl, 10 mM tris, pH 8.0) and recentrifuged. The mutant GGBP-His was eluted from the beads by adding 5 mL solution (160 mM imidazole, 1 M NaCl, 10 mM Tris, pH 8.0) and mixing for 15 min. The protein solution was immediately filtered through a Centriplus YM-100 filter (Amicon, Charlotte, N.C.) and then concentrated to 1-3 mg/ml using a Centriplus YM-10 filter. The protein was dialyzed overnight against 2 L of storage solution (1 M NaCl, 10 mM Tris, 50 mM NaPO$_4$, pH 8.0).

Example 3

Figure 1:
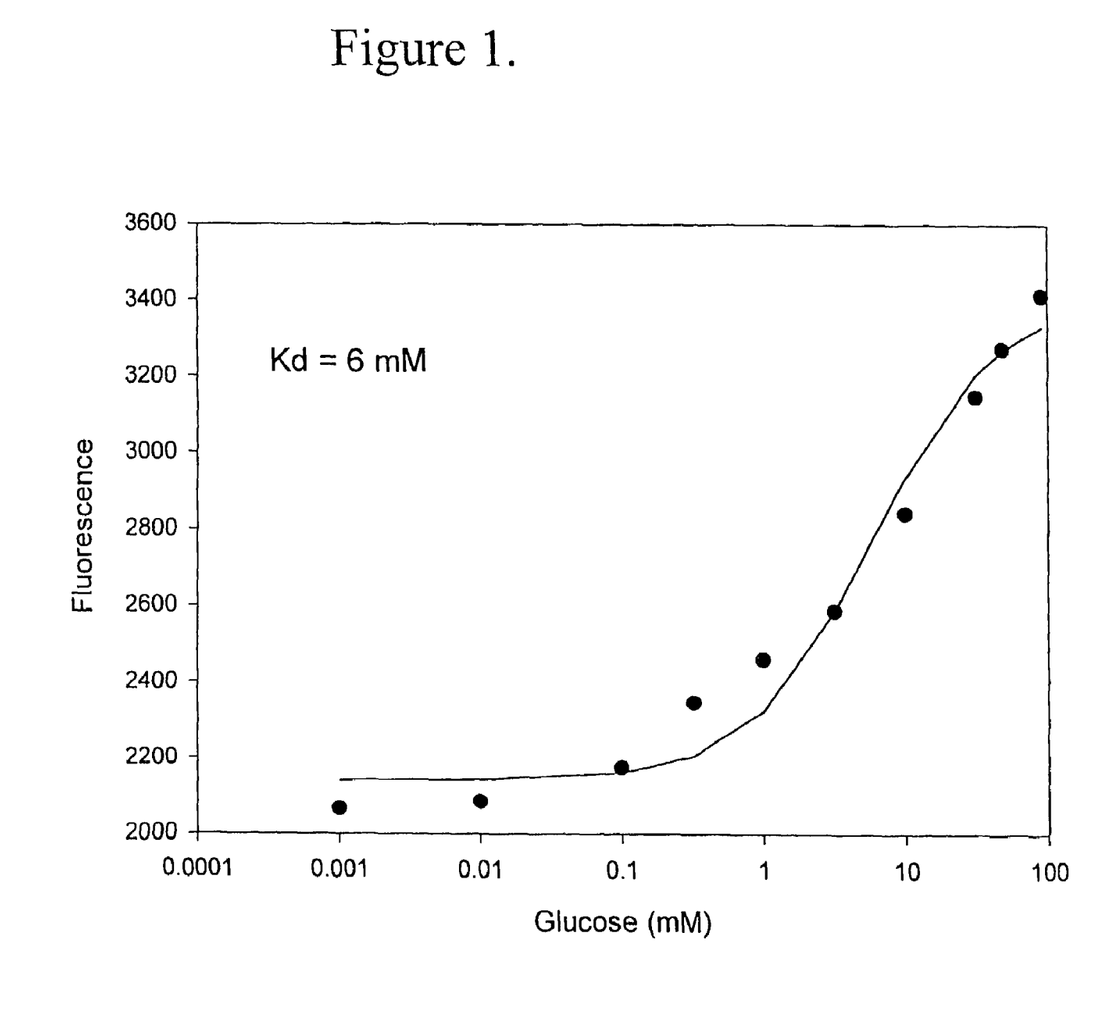
FIG. 1 illustrates the change in fluorescence response to glucose of A213C/L238C NBD amide GGBP $H_6$ in solution.

This example describes generically the labeling of binding protein with reporter probe. An aliquot of mutant GGBP containing cysteine (4.0 nmol) in PBS was treated with 2 mM dithiothreitol (5 µL, 10 nmol) for 30 min. A stock solution of N,N'-dimethyl-N-(iodoacetyl)-N'-(7-nitrobenz-2-oxa-1,3-diazol-4-yl)ethylenediamine (IANBD amide, 0.5 mg) was prepared in DMSO (100 µL, 11.9 mM) and 3.36 µL (40 nmol) was added to the protein. The reaction proceeded at room temperature for 4 h on a Dynal rotamix in the dark. The labeled protein was purified by gel filtration on a NAP-5 column (Amersham Pharmacia). The labeling rations were determined using an estimated extinction coefficient (50 mM$^{-1}$ cm$^{-1}$) for GGBP that was calculated in GeneWorks 2.45 (IntelliGenetics), $\epsilon_{478}$ (IANBD amide)=25 mM$^{-1}$cm$^{-1}$), and a measurement of O.D. for a standard solution of IANBD amide at 280 nm and 478 nm. The dye concentration in the protein was calculated as $C_{dye} = \gamma_{478}/A_{478}$. The absorbance of protein at 280 nm was calculated as $A_{prot(280)} = A_{total(280)} - A_{dye(280)}$, where $A_{dye(280)} = A_{478} \times (A_{280}/A_{478})$standard. The concentration of protein was then $C_{prot(280)} = \epsilon_{280}/A_{prot(280)}$. FIG. 1 illustrates the change in fluorescence response to glucose concentration of a representative example, A213C/L238C NBD amide GGBP H$_6$ in solution. Table 1 summarizes the change in fluorescence of various GGBP mutants labeled with reporter groups, including reporting groups having either excitation or emission maximum of at least 600 nanometers. Table 2 summarizes the change in fluorescence, and determined Kd values of mutations of one, two, three, and four amino acid substitutions. This data clearly shows mutations of the GGBP labeled with a reporter group can provide desirable attributes as glucose biosensors. The data shows the mutation-reporter group relationship for the samples tested.

TABLE 1

Percent Change in Fluorescence for GGBP Mutants[1]

| Dye | Excitation/emission (nm) | S112C | M182C | A213C | A213C His$_6$ | M216C |
| --- | --- | --- | --- | --- | --- | --- |
| IANBD amide | 470/550 | 0 | 4 | 3 | 51 | 7 |
| IANBD ester | 470/550 | | | | | |
| IAEDANS | 336/490 | −7 | −8 | 0 | | −9 |
| Bodipy530/550 IA | 530/550 | 7 | −10 | 33 | | 4 |
| XRIA 5,6 | 575/600 | −21 | −19 | −38 | | −15 |
| Lucifer Yellow IA | 426/530 | | | −14 | | −3 |
| Bodipy 507/545 IA | 507/545 | | | 25 | | −3 |
| Cy5 | 640/660 | 2 | 0 | 11 | | −7 |
| Texas Red-maleimide | 580/610 | | | | −13 | |
| Dapoxyl | 375/580 | 15 | 7 | 12 | | 2 |

[1]ΔF from 0 to 1 mM glucose at 0.5 uM [dye]. Unless otherwise indicated all mutants were without histidine tags.

TABLE 2

Summary of GGBP-H6 NBD Mutations

| Identification | Δ F(%)[1] | Solution Kd(mM)[2] | Dye/Prot | Seqncd |
|---|---|---|---|---|
| wild type | intrinsic | 0.0002 | — | for/rev |
| A1C | — | — | — | — |
| K11C | 10 | — | 1.8 | rev |
| D14C | 1 | — | 1.5 | rev |
| V19C | −56 | 0.0001 | 0.38 | — |
| N43C | 40 | 0.0002 | 0.28 | — |
| G74C | −3 | 0.0009 | 1.43 | — |
| Y107C | −30 | 0.001 | 0.93 | for |
| T110C | −9 | — | — | for/rev |
| S112C | 220 | 0.05 | 1.15 | — |
| S112C, L238S | 6 | — | 1.5 | — |
| K113C | 15 | — | 0.65 | — |
| K137C | −5 | 0.00004 | 1.17 | — |
| E149C | 300 | 0.0002 | 0.96 | — |
| E149C, A213R | 660 | 1 | 1.1 | for/rev |
| E149C, K223N | — | — | — | — |
| E149C, L238S | 660[4] | 0.08 | 1.36 | for/rev |
| E149C, N256S | 1 | — | 0.93 | for/rev |
| E149C, M182C, A213C, L238S | 200 | 216[6] | 3.2 | for/rev |
| E149C, A213S, L238S | 480 | 0.47 | 0.76 | for/rev |
| E149C, A213R, L238S | 500 | 35 | — | — |
| H152C, A213R | −3 | — | 1.2 | for/rev |
| H152C, A213S | 100 | 0.16 | — | — |
| H152C, K223N | 200 | 0.003 | 1 | for |
| M182C | 11 | — | — | for/rev |
| A213C | 50 | 0.124 | 0.68 | for/rev |
| A213C, L238C | 24, 67[3] | 6 | 1.4 | for/rev |
| M216C | 67 | 0.008 | 0.91 | for |
| L238C | −6, +3[3] | — | 1.3 | for/rev |
| D287C | 4 | — | 1.1 | for |
| R292C | −34 | 0.0008 | 1.5 | for |

[1]ΔF from 0 to 1 mM Glc at 0.5 μM [NBD]
[2]Kd measured at 0.1 μM [dye]
[3]ΔF when measured from 0 to 100 mM Glc
[4]ΔF when measured from 0 to 10 mM Glc
[5]Estimated; Sigma Plot calc. did not converge
[6]Estimated; curve did not reach saturation
Seqncd = sequencing, for = forward; rev = reversed; for/rev = both Example 4

This example describes the immobilization of a biosensor of the instant invention using glycerol modified silicate condensate (GMSC). The additions of glycerol directly followed the initial tetraethoxyorthosilicate (TEOS) or tetramethoxyorthosilicate (TMOS) acid hydrolysis. A range of hydrolysis times, pH levels, reagent addition order, and TEOS:glycerol ratios were evaluated to determine the optimal conditions for beginning the glyceration reaction. Preferred conditions were found using an interval of 10 to 30 minutes between hydrolysis and glycerol addition, a pH range of between 0.5 and 1, and a 1:1 mole ratio of TEOS to glycerol. The following describes a modified procedure of Gill and Ballesteros for a TEOS-based glycerol modified silicate condensate (GMSC) preparation using the following ratios of reagents: TEOS or TMOS:1; H2O:1, Methanol:4, Glycerol:1. TEOS or TMOS in methanol was added to a flask and cooled to 0° C. over ice. Next 0.6M HCl was added drop-wise to the solution. After 20 minutes of stirring, glycerol was added dropwise. The reaction was warmed slowly over 1-2 hours to 20-25° C. Following this the reaction vessel was heated further and maintained at a temperature range of 60-70° C. under nitrogen for between 36 and 42 hours. The optimal time was 40 hours. Incomplete glyceration was indicated by an observable phase separation for reactions stopped before 36 hours. Reactions maintained beyond 42 hours produced GMSC sol-gel monoliths with greatly reduced physical properties, for example, increased brittleness. Following the 40 hour reaction at 60-70° C., the solution volume was reduced by rotary evaporation until it was viscous and transparent, at which point methanol was added to the solution in a 4:1 ratio by weight. This GMSC solution proved to be stable and provided consistent results for several months when stored at freezer temperature. When the GMSC solution was to be used, methanol was removed by rotary evaporation and distilled water was added in a 1:1 ratio by weight to the GMSC reagent to catalyze the final hydroylsis/gelation. Monoliths, thin films, and powders were created with this procedure using an appropriate container to function as a mold. The GMSC sol-gel monoliths were not brittle and had shrinkage of about 8% after curing at 4° C. at 50% relative humidity for 2 weeks (% shrinkage was the average of changes in diameter and length measured with a microcaliper and compared to original mold dimensions). Electron microscopy (SEM) further illustrated the significant improvements in surface fracturing between monoliths created with TEOS hydrolysis and the monoliths created through the GMSC procedure described above. This set of experiments demonstrates how sol-gels with improved physical characteristics can be produced in accordance with the methods taught in the instant invention.

Example 5

This example describes further optimization of physical properties by GMSC sol-gels in which glycerol has been partly substituted with either ethylene glycol (EG) or polyethylene glycol (PEG). Ethylene glycol (EG) was evaluated as a substitute for glycerol in mixtures where the ratio of glycerol and EG was varied but the mole ratio of total glycerol and EG was maintained constant relative to other reagents. Sol-gel monoliths were prepared by the procedure described in the preceding example, cured for two weeks at 4° C. and 50% relative humidity and their % shrinkage was determined and stated in Table 3. % Shrinkage is defined as the average of the decrease in length and diameter versus original dimensions. Monoliths used for determination of shrinkage had no protein/fluorophore present. For ΔF measurements, the samples listed in Table 1 were prepared containing H152 GGBP-H6 NBD (from Example 3) as will be described shortly.

TABLE 3

Average % shrinkage and ΔF of sol-gel Matrix after 2 weeks.

| Sol-gel Matrix | Average % shrinkage | ΔF (10 mM Glucose) |
|---|---|---|
| 1. Solution (H152 GGBP-H6 NBD 0.8-1.2 uM) | Not Applicable | 1.53 |
| 2. TEOS | 35.95 +/− 0.24 | 1.39 |
| 3. GMSC-TEOS | 8.01 +/− 0.19 | 1.57 |
| 4. GMSC-TEOS 15 wt % PMSA, 0.145 mol % MTMOS | 3.99 +/− 0.27 | — |
| 5. 1% EG/GMSC-TEOS | 3.10 +/− 0.17 | 1.53 |
| 6. 5% EG/GMSC-TEOS | 2.48 +/− 0.15 | 1.47 |

TABLE 3-continued

Average % shrinkage and ΔF of sol-gel Matrix after 2 weeks.

| Sol-gel Matrix | Average % shrinkage | ΔF (10 mM Glucose) |
|---|---|---|
| 7. 10% EG/GMSC-TEOS | — | 1.37 |
| 8. 20% EG/GMSC-TEOS | — | 1.34 |

The 1% and 5% EG/GMSC sol-gels (entries 5 and 6 respectively in Table 3) were found to have significantly less % shrinkage than either the plain TEOS sol-gels or GMSC modified TEOS sol-gels (entries 2 and 3 respectively in above Table 3). Polyethylene Glycol (PEG) was also evaluated qualitatively as a partial substitute for glycerol in similar proportions in GMSC sol-gels and produced monoliths with favorable surface properties and rubber-like flexibility. In summary, partial substitution of either ethylene glycol (EG) or polyethylene glycol (PEG) for glycerol in GMSC sol-gels provides improvements in physical properties, for example, minimized shrinkage and reduced surface fracturing. These sol-gel matrixes containing binding protein were found to possess performance equal to or better than that of protein in solution.

Example 6

Figure 2:
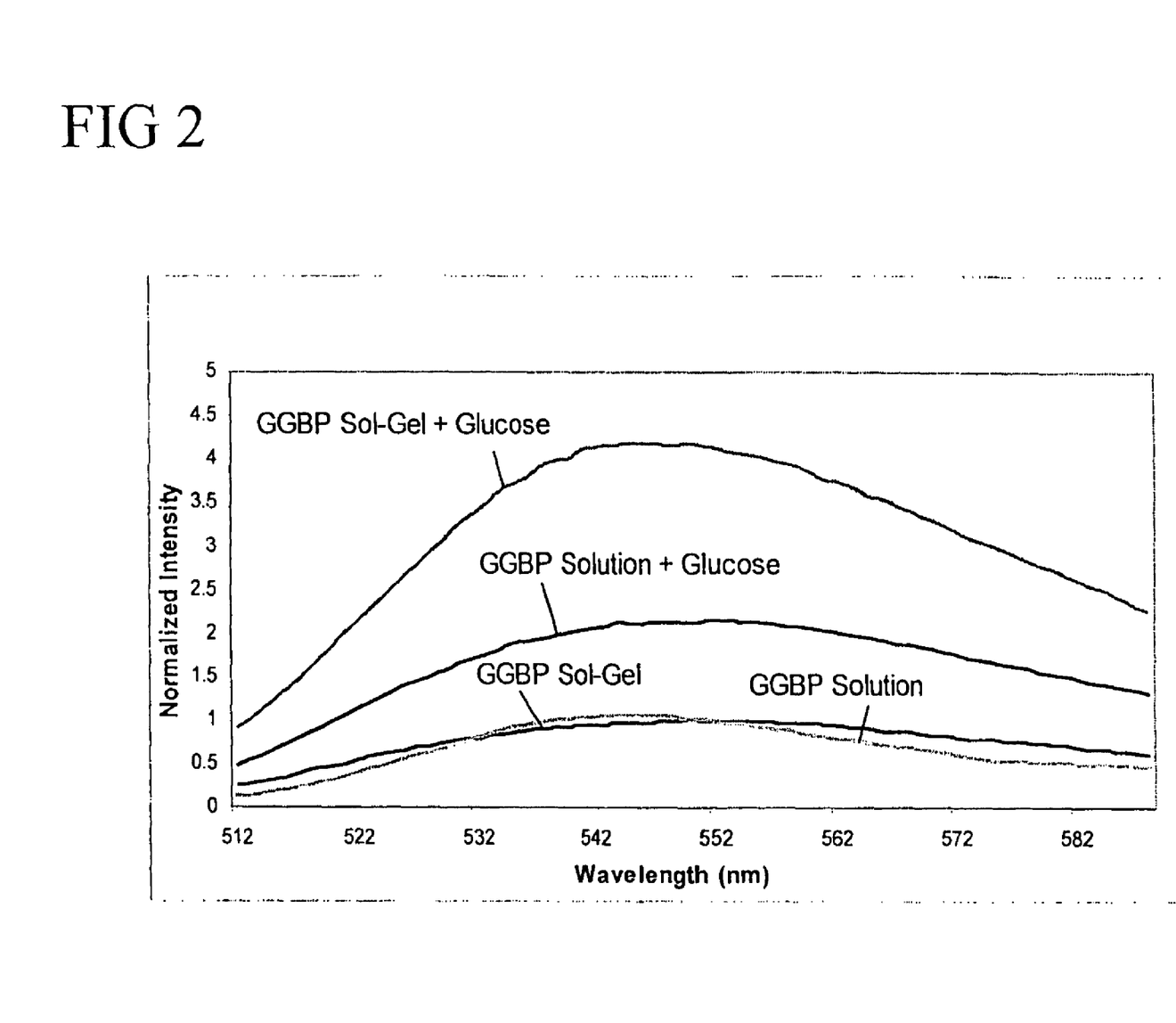
FIG. 2 illustrates signal enhancement of entrapped binding proteins in the absence and presence of analyte relative to solution.

Entrapment Of Binding Proteins In GMSC Sol-Gels Containing Functionalized Silicone Additives (FSA) and Polymers. This example describes the addition of polymer and organic polyol additives to optimize the GMSC sol-gels for entrapping binding proteins to both maintain and enhance their spectral properties upon ligand binding. The binding proteins were labeled with a fluorophore (as described in example 3). The protein solutions were added during the final hydrolysis/gelling step described previously to produce final concentrations of 2-4 μM protein within the sol-gel. The polymer additives and FSA's were obtained from Sigma-Aldrich Chemicals (St. Louis, Mo.). Polymer additives were evaluated in amounts between 0 to about 30 wt. Functionalized silicone additives (FSA) were evaluated as additives to the GMSC sol-gels in amounts from 0 to about 0.6% mole ratio. Thus, rotary evaporation of the GMSC reagent to remove methanol from its storage solution was followed by reconstitution in water in a 1:1 ratio by weight. To a 400 μL aliquot of this mixture, 800 μL of buffer (HEPES, PBS or Tris) with a premixed water soluble polymer additive was added along with any FSA-modified GMSC. A mutated binding protein in solution was then, and after thorough mixing, 100 μL of the mixture was dispensed into a 96 well microplate (Falcon white flat bottom plates, product # 35-3941, BD Labware, N.J.). The sol-gel containing microplates were cured 12-18 hours at 4° C. and 50% relative humidity. GMSC-BIS was prepared by the same procedure as the TEOS-based GMSC, but with substitution of (Bis(3-methyldimethoxysilyl)propyl) polypropylene oxide for TEOS. GMSC-MTMOS and GMSC-ATEOS were prepared similarly except that the hydrolysis was carried out with either 10% of the amount of acid, or no acid in the hydrolysis step, respectively compared to the TEOS-based GMSC procedure. Fluorescence emission was measured with a Varian Cary Eclipse scanning fluorometer with microwell plate adapter (Varian Instruments, Victoria, Australia). Excitation was at 475 nm and emission recorded from 500 to 600 nm, typically monitoring emission maximum peak fluorescence. Slit widths were 5 nm for excitation and 10 nm for emission. Individual $I_o$ determinations were made for each well and 100 μL of a ligand solution (1 mM maltose in the case of S337C MBP, and 10 mM glucose in the case of H152C GGBP, or 100 mM glucose in the case of A213C/L238C) was added and $I_f$ readings were obtained, from which ΔF values were calculated. The modified sol-gel entrapped proteins exhibited greater initial fluorescence ($I_o$) in the absence of ligand when compared to equivalent concentrations of the same protein in solution. FIG. 2 shows the fluorescence emission before and after glucose addition for GGBP H152 His6 NBD in the H152 optimized sol-gel and in solution. The $I_o$ spectra for each experiment was normalized to a maxima of 1.0. The figure shows about 2-3-fold enhancement of ΔF obtained for the optimized sol-gel matrixes containing binding protein when exposed to analyte in comparison to protein in solution. Thus, after optimization of the sol-gel formulations for each protein, an enhancement of ΔF was observed. It should be noted that emission maximum may be shifted for sol-gel entrapped protein-reporter group samples as compared to solution. In addition, these modified sol-gel matrixes provide improved physical properties as shown in entry 4 of Table 3. Table 4 shows an approximate range of components of formulations giving improved response for each of the individual proteins evaluated.

TABLE 4

Optimized sol-gel formulations for H152C GGBP His6-NBD, A213C/L238C GGBP His6-NBD, and S337C-MBP-NBD. (GGBP = glucose/galatose binding protein; MBP = maltose binding protein; NBD = N-(acetoxy)ethyl)-N-methyl)amino-7-nitrobenzoxadiazole.

| | | H 152 C GGBP-NBD | | A213C/L238C GGBP-NBD | | S337C MBP-NBD |
|---|---|---|---|---|---|---|
| | | Range | | Range | | Range |
| Polymer additive | PMSA | 14-16% wt | PMSA | 4-6% wt | PMSA | 14-16% wt |
| FSA additive | Alkyl | 0.13-0.16 mol % | Alkyl | 0.01-0.03 mol % | Amine | 0.01-0.03 mol % |
| Buffer | Tris | | PBS | | PBS | |
| pH Range | | 7.3-7.5 | | 7.4-7.7 | | 7.4-7.7 |
| Kd (mM) | | 0.36 | | 2.2 | | — |
| [solution value] | | [0.07] | | [6] | | |
| ΔF (enhancement vs. solution) [sugar challenge] | | 2.93x [10 mM] | | 2.36x [100 mM] | | 2.53x [0.1 mM] |

The formulation optimization experiments described above used Design-Expert 6.0.5 (Stat-Ease, Inc., Minneapolis, Minn.) to design several Design of Experiments (DOE's). Among other variables in formulation which were optimized in each DOE were buffer type (HEPES, PBS and Tris) and pH (from 6.6 to 7.8). Surprisingly, the optimal formulation constituents and concentration ranges were quite different for each protein. In all cases, however, substantial performance improvements were obtained for the optimized formulations in comparison to either solution performance or performance in unmodified sol-gels.

Example 7

Figure 3:
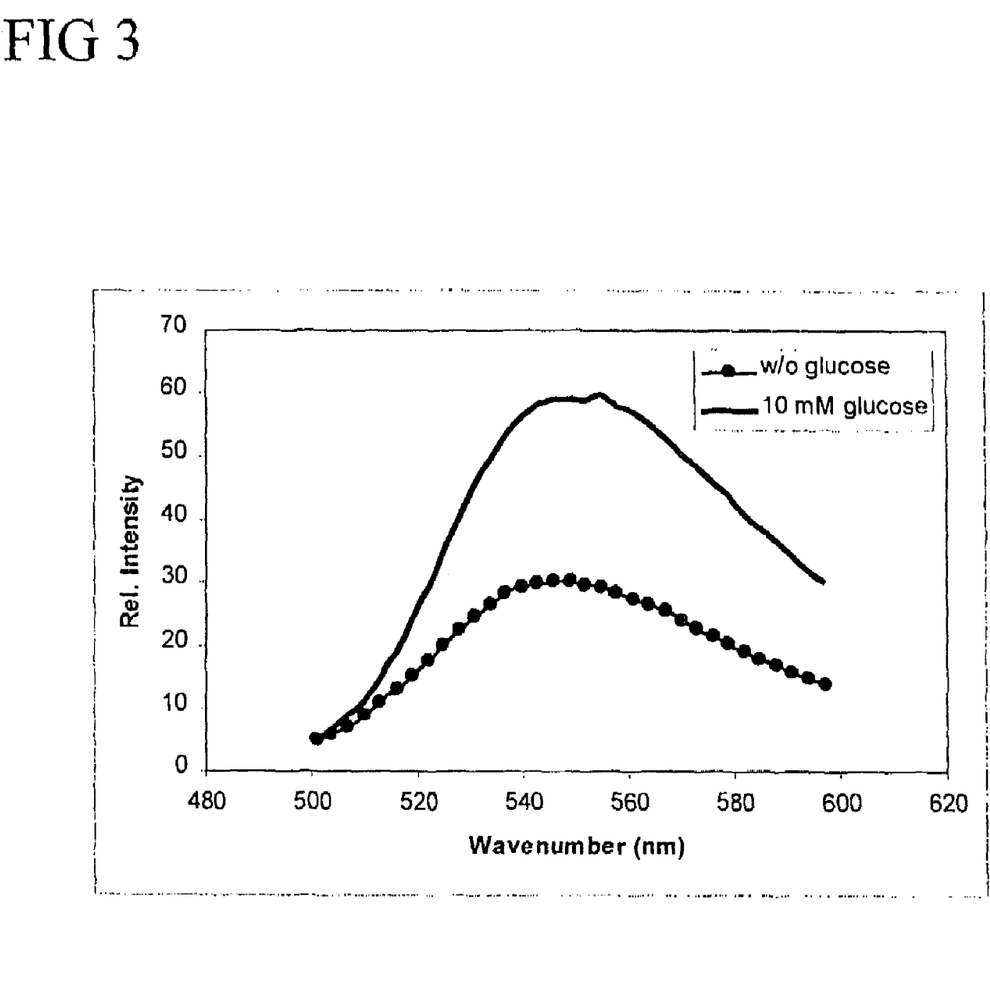
FIG. 3 illustrates an entrapped binding protein in the absence and presence of analyte relative to solution.

This example describes the entrapment of GGBP H152C in UV cross-linked hydrogel matrix and the effect of the matrix on the fluorescence change and binding affinity. In this experiment SbQ-PVA from Polysciences Inc. was added 100 ul of PBS buffer and mixed for one hour to mix in a rotary mixer. 80 ul of this solution was then mixed with 20 ul of labeled protein. Final protein concentration was spectroscopically determined to be 0.15 mg/ml. After mixing, aliquiots were dispensed into 96-well plates and dried in a chamber maintained at 20% humidity for 12 h followed by curing with UV light. Wells containing protein encapsulated in matrix were challenge with 2 ul of 10 mM glucose and compared to protein solution without matrix having equivalent protein loading. FIG. 3 shows the ability of the mutated protein matrix to respond to the analyte in a manner, and with a sensitivity, equivalent to that obtained in solution. The Kd of the entrapped protein was comparable to that obtained in solution.

Example 8

Figure 4:
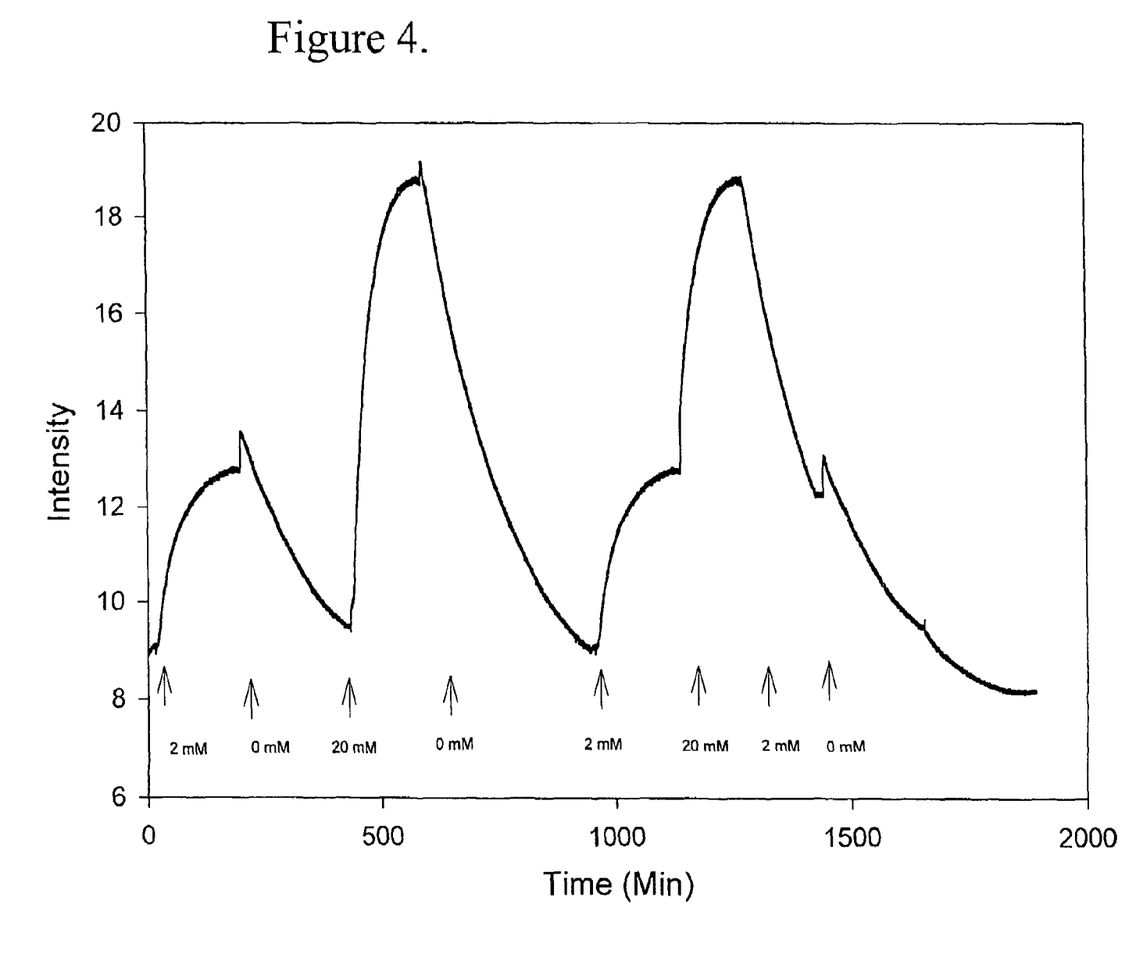
FIG. 4 illustrates reversible signal from an entrapped binding protein from one embodiment of the present invention.

This example describes the immobilization of a biosensor of the instant invention into a dialysis membrane matrix and the ability of the matrix to provide reversible and continuous readings. Using a Varian Eclipse fluorimeter with a fiber optic attachment, GGBP L238C/A213C protein (2 μM in PBS buffer) entrapped within a dialysis membrane having a molecular cut-off of 3500 Daltons affixed to the distal end of the fiber. Solutions were prepared containing PBS buffer, 2 mM, and 20 mM glucose in PBS buffer. With the probe in PBS solution, readings were recorded at 0.02 seconds intervals of the emission wavelength 521 nm, followed by insertion of the fiber into the glucose solutions. Replacement of the fiber into buffer-only solution resulted in the return of initial signal. FIG. 4 depicts multiple cycles alternating between buffer and glucose solutions demonstrating the reversibility of the biosensor entrapped within a permeable matrix within physiological range. Similar results were observed with sol-gel entrapped samples demonstrating applicability for continuous use.

We claim:

1. A glucose biosensor for in vivo or in vitro use comprising:
    a) at least one mutant glucose/galactose binding protein (GGBP) and at least one reporter group covalently attached thereto wherein said mutant GGBP comprises at least one amino acid substitution of a non-reactive amino acid with a reactive amino acid, wherein said at least one amino acid substitution is selected from the group consisting of a cysteine at position 11, a cysteine at position 14, a cysteine at position 19, a cysteine at position 43, a cysteine at position 74, a cysteine at position 107, a cysteine at position 110, a cysteine at position 112, a cysteine at position 113, a cysteine at position 137, a cysteine at position 149, a cysteine at position 213, a cysteine at position 216, a cysteine at position 238, a cysteine at position 287, a cysteine at position 292, a cysteine at position 112 and a serine at position 238, a cysteine at position 149 and a serine at position 238, a cysteine at position 152 and a cysteine at position 182, a cysteine at position 152 and a serine at position 213, a cysteine at position 213 and a cysteine at position 238, a cysteine at position 149 and an arginine at position 213, a cysteine at position 149 and a serine at position 213 and a serine at position 238, and a cysteine at position 149 and an arginine at position 213 and a serine at position 238 corresponding to amino acid positions of E. coli GGBP, and
    b) a first analyte permeable matrix entrapping or encapsulating said at least one mutant GGBP, said matrix comprising a covalently crosliniked hydrogel or a sol-gel comprising organically modified silicates or a combination thereof, wherein the first analyte permeable matrix is formulated to allow three-dimensional conformational movement of the at least one mutant GGBP to bind and release the glucose, and wherein the matrix is adapted to allow glucose to diffuse into and out of the matrix.

2. The biosensor of claim 1 wherein said reporter group provides a detectable and reversible signal that is related to said varying analyte concentrations.

3. The biosensor of claim 1 wherein said mutant GGBP has at least one histidine tag.

4. The biosensor of claim 1 wherein said reporter group is a luminescent label.

5. The biosensor of claim 4 wherein said luminescent label has an excitation wavelength of more than about 600 nanometers.

6. The biosensor of claim 4 wherein said luminescent label has an emission wavelength of more than about 600 nanometers.

7. The biosensor of claim 1 wherein said luminescent label is covalently coupled to said at least one mutant glucose/galactose binding protein by reaction with a member selected from the group consisting of fluorescein, coumarins, rhodamines, 5-TMRIA (tetramethylrhodamine-5-iodoacetamide), Quantum Red™, Texas Red™, Cy3, N-((2-iodoacetoxy)ethyl)-N-methyl)amino-7-nitrobenzoxadiazole (IANBD), 6-acryloyl-2-dimethylaminonaphthalene (acrylodan), pyrene, Lucifer Yellow, Cy5, Dapoxyl® (2-bromoacetamidoethyl)sulfonamide, (N-(4,4-difluoro-1,3,5,7-tetramethyl-4-bora-3a,4a-diaza-s-indacene-2-yl)iodoacetamide (Bodipy507/545 IA), N-(4,4-difluoro-5,7-diphenyl 4-bora-3a,4a-diaza-s-indacene-3-propionyl)-N-iodoacetylethylenediamine (BODIPV® 530/550 IA), 5-((((2-iodoacetyl)amino) ethyl)amino)naphthalene-1-sulfonic acid (1,5-1AEDANS), and carboxy-X-rhodamine, 5/6-iodoacetamide (XRIA 5,6).

8. The biosensor of claim 1, wherein said matrix is a covalently crosslinked hydrogel, wherein said covalently crosslinked hydrogel is selected from the group consisting of polypeptides, polysaccharides, polysaccharide derivatives, polyvinyl alcohol, polyacrylic acid, polyacrylamide, polyethylene glycols, copolymers of styrene and maleic anhydride, copolymers of olefin and maleic anhydride, and copolymers or vinyl ether and maleic anhydride.

9. The biosensor of claim 8 wherein said polyvinyl alcohol includes poly(vinyl alcohol), N-methyl-4(4'-formylstyryl) pyridinium acetal salts.

10. The biosensor of claim 1 further comprising at least one water soluble polymer component.

11. The biosensor of claim 10 wherein said at least one water soluble polymer component is selected from polyvinyl alcohol, copolymers of styrene and maleic anhydride, copolymers of olefin and maleic anhydride, and copolymers of vinyl ether and maleic anhydride, poly-(vinylsulfonic acid) salt, and polyvinyl pyrollidone.

12. The biosensor of claim 1 wherein said organically modified silicates comprise organic functionality selected from the group consisting of alkyl, aryl, amine, amide, thiol, cyano, carboxyl, ester, olefinic, epoxy, silyl, nitro, and halogen.

13. The biosensor of claim 1, wherein the matrix is a glycerol modified silicate condensate (GMSC)-derived sol-gel.

14. The biosensor of claim 13, wherein said first analyte permeable matrix is contained within an additional analyte permeable matrix, wherein said additional analyte permeable matrix is a hydrogel, a sol-gel or a dialysis membrane.

15. A glucose biosensor for in vivo or in vitro use comprising:
    a) at least one mutant glucose/galactose binding protein (GGBP) and at least one reporter group covalently attached thereto wherein said mutant GGBP comprises at least one amino acid substitution of a non-reactive amino acid with a reactive amino acid, and
    b) a first analyte permeable matrix entrapping or encapsulating said at least one mutant GGBP, said matrix comprising a covalently crosslinked sol-gel comprising organically modified silicates, wherein said sol-gel is selected from at least partially cured hydrolytically condensable siloxanes condensed with at least one water soluble organic polyol component, wherein the first analyte permeable matrix is formulated to allow three-dimensional conformational movement of the at least one mutant GGBP to bind and release the glucose, and wherein the matrix is adapted to allow glucose to diffuse into and out of the matrix.

16. The biosensor of claim 15 wherein said reporter group provides a detectable and reversible signal that is related to said varying analyte concentrations.

17. The biosensor of claim 15 wherein said mutant GGBP has at least one histidine tag.

18. The biosensor of claim 15 wherein said reporter group is a luminescent label.

19. The biosensor of claim 18 wherein said luminescent label has an excitation wavelength of more than about 600 nanometers.

20. The biosensor of claim 18 wherein said luminescent label has an emission wavelength of more than about 600 nanometers.

21. The biosensor of claim 15 wherein said luminescent label is covalently coupled to said at least one mutant glucose/galactose binding protein by reaction with a member selected from the group consisting of fluorescein, coumarins, rhodamines, 5-TMRIA (tetramethylrhodamine-5-iodoacetamide), Quantum Red™, Texas Red™, Cy3, N-((2-iodoacetoxy)ethyl)-N-methyl)amino-7-nitrobenzoxadiazole (IANBD), 6-acryloyl-2-dimethylaminonaphthalene (acrylodan), pyrene, Lucifer Yellow, Cy5, Dapoxyl® (2-bromoacetamidoethyl)sulfonamide, (N-(4,4-difluoro-1,3,5,7-tetramethyl-4-bora-3a,4a-diaza-s-indacene-2-yl)iodoacetamide (Bodipy507/545 IA), N-(4,4-difluoro-5,7-diphenyl 4-bora-3a,4a-diaza-s-indacene-3-propionyl)-N-iodoacetylethylenediamine (BODIPV® 530/550 IA), S-((((2-iodoacetyl)amino) ethyl) amino)naphthalene-1-sulfonic acid (1,5-1AEDANS), and carboxy-X-rhodamine, 5/6-iodoacetamide (XRIA 5,6).

22. The biosensor of claim 15 wherein said at least one water soluble organic polyol component is selected from the group consisting of glycerol, ethylene glycol, propylene glycol, and polyethylene glycol.

23. The biosensor of claim 15 further comprising at least one water soluble polymer component.

24. The biosensor of claim 23 wherein said at least one water soluble polymer component is selected from polyvinyl alcohol, copolymers of styrene and maleic anhydride, copolymers of olefin and maleic anhydride, and copolymers of vinyl ether and maleic anhydride, poly-(vinylsulfonic acid) salt, and polyvinyl pyrollidone.

25. The biosensor of claim 15 wherein said organically modified silicates comprise organic functionality selected from the group consisting of alkyl, aryl, amine, amide, thiol, cyano, carboxyl, ester, olefinic, epoxy, silyl, nitro, and halogen.

26. The biosensor of claim 15, wherein the matrix is a glycerol modified silicate condensate (GMSC)-derived sol-gel.

27. The biosensor of claim 15, wherein said first analyte permeable matrix is contained within an additional analyte permeable matrix, wherein said additional analyte permeable matrix is a hydrogel, a sol-gel or a dialysis membrane.

28. The biosensor of claim 15, wherein said at least one amino acid substitution is selected from the group consisting of a cysteine at position 11, a cysteine at position 14, a cysteine at position 19, a cysteine at position 43, a cysteine at position 74, a cysteine at position 107, a cysteine at position 110, a cysteine at position 112, a cysteine at position 113, a cysteine at position 137, a cysteine at position 149, a cysteine at position 213, a cysteine at position 216, a cysteine at position 238, a cysteine at position 287, a cysteine at position 292, a cysteine at position 112 and a serine at position 238, a cysteine at position 149 and a serine at position 238, a cysteine at position 152 and a cysteine at position 182, a cysteine at position 152 and a serine at position 213, a cysteine at position 213 and a cysteine at position 238, a cysteine at position 149 and an arginine at position 213, a cysteine at position 149 and a serine at position 213 and a serine at position 238, and a cysteine at position 149 and an arginine at position 213 and a serine at position 238 corresponding to amino acid positions of *E. coli* GGBP.

* * * * *

UNITED STATES PATENT AND TRADEMARK OFFICE
CERTIFICATE OF CORRECTION

| | | |
|---|---|---|
| PATENT NO. | : 7,629,172 B2 | Page 1 of 1 |
| APPLICATION NO. | : 10/949557 | |
| DATED | : December 8, 2009 | |
| INVENTOR(S) | : Javier Alarcon et al. | |

It is certified that error appears in the above-identified patent and that said Letters Patent is hereby corrected as shown below:

Column 22, line 9, replace "S-((((2-iodoacetyl)amino)" with -- 5-((((2-iodoacetyl)amino) --

Signed and Sealed this

Eleventh Day of May, 2010

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,629,172 B2 |
| APPLICATION NO. | : 10/949557 |
| DATED | : December 8, 2009 |
| INVENTOR(S) | : Javier Alarcon et al. |

It is certified that error appears in the above-identified patent and that said Letters Patent is hereby corrected as shown below:

On the title page, Item (*) Notice should read:

Subject to any disclaimer, the term of this patent is extended or adjusted under 35 U.S.C. 154(b) by 1079 days.

Signed and Sealed this

Seventeenth Day of August, 2010

David J. Kappos
*Director of the United States Patent and Trademark Office*